(12) United States Patent
Wild et al.

(10) Patent No.: US 6,426,440 B1
(45) Date of Patent: Jul. 30, 2002

(54) METHOD FOR PREPARING DECOMPOSITION PRODUCTS FROM THE THERMAL DECOMPOSITION OF 1,2-DICHLORETHANE

(75) Inventors: Thomas Wild, Burgkirchen; Juergen Eichler, Kastl; Werner Strang; Peter Widmann, both of Burgkirchen, all of (DE)

(73) Assignee: Vinnolit Monomer GmbH & Co. KG, Ismaning (DE)

( * ) Notice: Subject to any disclaimer, the term of this patent is extended or adjusted under 35 U.S.C. 154(b) by 0 days.

(21) Appl. No.: 09/673,998

(22) PCT Filed: May 4, 1998

(86) PCT No.: PCT/EP98/02611

§ 371 (c)(1),
(2), (4) Date: Dec. 26, 2000

(87) PCT Pub. No.: WO99/57088

PCT Pub. Date: Nov. 11, 1999

(51) Int. Cl.$^7$ .......................... C07C 17/00; C07C 17/25
(52) U.S. Cl. ....................... 570/207; 570/208; 570/209; 570/210; 570/220; 570/226
(58) Field of Search ................................. 570/207, 208, 570/209, 210, 222, 226

(56) References Cited

FOREIGN PATENT DOCUMENTS

DE          41 39 632 A1  *  3/1993

* cited by examiner

*Primary Examiner*—Alan Siegel
(74) *Attorney, Agent, or Firm*—Frommer Lawrence & Haug LLP; Ronald R. Santucci

(57) ABSTRACT

The work-up of the gaseous products from the thermal cracking of 1,2-dichloroethane is simplified if the cracking gases are cooled to a temperature range of about 150 to 180° C., only a subsidiary proportion, which comprises all the coke formed, being condensed and fed to a separate work-up.

5 Claims, No Drawings

METHOD FOR PREPARING DECOMPOSITION PRODUCTS FROM THE THERMAL DECOMPOSITION OF 1,2-DICHLORETHANE

This application is a 371 of PCT/EP98/02611 filed May 4, 1998.

DESCRIPTION

Vinyl chloride ("VC" below) is prepared industrially by thermal cracking of 1,2-dichloroethane ("EDC" below) at temperatures of 450 to 600° C. at elevated pressure. In this process, about 40 to 65% of the feed EDC is cracked into VC and hydrogen chloride. In this cracking, by-products having higher and lower boiling points than the EDC are formed. Multistage separation by distillation must therefore be carried out.

The gaseous products of the thermal cracking (cracking gas) are first passed through a filter to remove relatively coarse coke particles, condensed and passed into the first distillation column (HCl column), in which the hydrogen chloride is distilled off as overhead product. In a further column (VC column) the VC is distilled off as overhead product. The bottom phase of this column comprises the unreacted EDC and lower- and higher-boiling by-products and relatively fine coke particles.

These coke particles interfere in particular with the necessary removal of the benzene, so that to date complex fractionation of the bottom product and purification of the partial stream which were fed to the benzene removal stage have been necessary. Preferably, this fractionation and partial purification were performed by flash evaporation.

DE-A-40 33 047 discloses a process for removing benzene from the EDC recovered during VC preparation, after the separation of VC and hydrogen chloride, which is characterized in that the EDC from the column bottom of the VC column is divided into a product stream purified from high-boiling substances and an unpurified product stream, the purified product stream is treated with chlorine in the presence of metallic iron at a temperature of 30 to 85° C. and this product stream is recombined with the unpurified product stream and the EDC is conjointly separated off from the high-boilers in a further purification step. An improvement of this process is that the catalyst used is γ-aluminium oxide (DE A-41 2 9 391).

DE-A-41 39 632 further discloses a process for removing benzene from the EDC recovered in the VC preparation downstream of the separation of the VC and hydrogen chloride, which is characterized in that the contaminated EDC from the column bottom of the VC column is separated into a product stream I freed from high-boiling substances (b.p.>83.7° C. 760 mmHg) and a product stream II containing the high-boiling substances (b.p.>83.7° C. 760 mmHg), the product stream I is treated with chlorine in the presence of metallic iron at a temperature of 30 to 85° C. and the treated product stream I is combined with the product stream II and the combined product streams are conjointly treated with chlorine at a temperature of 30 to 85° C. and purified EDC is separated off from this product stream in a distillation zone.

DE-A-41 32 761 discloses a process for working up the cracking gas which is produced in the thermal cracking of EDC to give VC at a temperature of 480 to 540° C. and a pressure of 15 to 25 bar and is cooled to a temperature of 180 to 280° C. if appropriate in a heat recovery stage and at this temperature is passed into a quench zone in which it is cooled and scrubbed by condensed cracking gas, which is characterized in that a) 80 to 99% by weight of the cooled cracking gases are taken off in the gaseous state as overhead product and 1 to 20% by weight of the cooled cracking gases are taken off as liquid bottom product of the quench zone, b) the coke present in the bottom product of the quench is comminuted, c) the dispersion produced in this case is separated in a stripping zone into a distillate and a bottom phase and the bottom phase from the process is ejected and d) the distillate of the stripping zone is combined with the gaseous overhead product of the quench zone after its condensation. Preferably, 3 to 6% by weight are taken off as bottom product from the quench zone.

It has now been found that the following mode of operation of the quench is suitable for considerably simplifying benzene chlorination: the fractionation of the product streams and the purification of one of these product streams can then be omitted, if the gaseous products from the thermal cracking of EDC are cooled to a relatively narrow, low temperature range of about 150 to 180° C., preferably 160 to 170° C., so that, in this condensation stage, only a small proportion of EDC, together with high-boiling fractions and coke formed, condenses. The majority of the unreacted EDC is thus passed together with the products VC and hydrogen chloride to the work-up by distillation, firstly the hydrogen chloride, and in a further stage, the VC, being separated off from the EDC by distillation, in a manner known per se. The residual EDC can then, without purification, be passed to the plant for removing benzene which is expediently performed using γ-aluminium oxide in accordance with the process of DE-A-41 29 391.

It is generally sufficient to subject only a portion of the EDC to the benzene chlorination in order to obtain a sufficiently low content of benzene and its secondary products in the EDC and VC. However, for the fractionation into partial streams, according to the invention a simple apparatus such as a control valve is sufficient.

According to the invention, less than 7%, preferably less than 5%, of the EDC can be condensed, so that only a relatively small proportion of coke-containing condensate must be worked up separately. Furthermore, the flash evaporation required in the known benzene chlorination process can be omitted, so that the process according to the invention is considerably less complex.

The invention is described in more detail in the following example.

EXAMPLE

The cracking gas from the EDC cracking is cooled with cracking gas condensate in the quench to about 160 to 170° C., 4% of the cracking gas condensing. All of the coke is present in the condensate. This coke is taken off and worked up separately.

The uncondensed roughly 96% of the cracking gas passes overhead in the gaseous state to the quench and is passed to the intermediate condensation and is condensed there. This condensate is likewise passed to the HCl column. In the subsequent distillation in the HCl and VC column, the column bottom phases are coke-free. The bottom stream from the VC column, after cooling to about 30 to 50° C., is divided by a control valve into two partial streams: roughly 8 t/hour pass into the benzene chlorination, about 20 t/hour bypass the benzene chlorination reactor and are combined with the product from this reactor. The combined product stream is passed without cooling to the chloroprene chlorination and passes from there to the high-boiler column.

In the procedure according to the invention, the plant sections associated with the flashing and filtration are thus omitted.

What is claimed is:

1. Process for working up the cracking products from the thermal cracking of 1,2-dichloroethane, wherein the gaseous products are cooled to a temperature range of 150 to 180° C., the uncondensed predominant proportion consisting of the cracking products HCl and VC and the unreacted 1,2-dichloroethane is fed to the work-up by distillation and the unreacted 1,2-dichloroethane is fed without further purification for benzene chlorination and the subsidiary proportion which comprises all of the coke is subjected to a separate work-up.

2. Process according to claim 1, wherein the cooling is carried out to a temperature range of 160 to 170° C.

3. Process according to claim 1, wherein less than 7% of the cracking gas is condensed.

4. Process according to claim 2, wherein less than 7% of the cracking gas is condensed.

5. Process according to claim 1, wherein only partial stream of the unreacted 1,2-dichloroethane is fed to the benzene chlorination.

* * * * *